United States Patent [19]
Schatz et al.

[11] Patent Number: 5,159,066
[45] Date of Patent: Oct. 27, 1992

[54] RECOMBINATION ACTIVATING GENE (RAG-1)

[75] Inventors: David G. Schatz, Cambridge; Marjorie A. Oettinger, Boston; David Baltimore, Cambridge, all of Mass.

[73] Assignee: Whitehead Institute for Biomedical Research, Cambridge, Mass.

[21] Appl. No.: 368,263

[22] Filed: Jun. 19, 1989

[51] Int. Cl.$^5$ .................... C07H 17/00; C12N 15/04
[52] U.S. Cl. .................................... 536/27; 435/172.3
[58] Field of Search ....................... 536/27; 435/172.3

[56] References Cited

PUBLICATIONS

Schatz, et al., Cell 59:1035–1048, 1989.
Chemical Absts. 114:76265h, 1991.
Chemical Absts. 113:185724g, 1990.
Halligan, Brian D. and Stephen V. Desiderio, *Proc. Natl. Acad. Sci. USA* 84:7019–7023 (1987).
Weaver, David and David Baltimore, *Proc. Natl. Acad. Sci. USA* 84:1516–1520 (1987).
Aguilera, Renato J. et al., *Cell* 51:909–917 (1987).
Desiderio, Stephen and David Baltimore, *Nature* 308:860–862 (1984).
Hope, Thomas J. et al., *Science* 231:1141–1145.
Kataoka, Tohru et al., *Nucl. Acids. Res.* 12:5995–6–10 (1984).
Lieber, Michael R. et al., *Genes & Development* 1:751–761 (1987).
Schatz, David. G. and David Baltimore, *Cell* 53:107–155 (1988).

*Primary Examiner*—John W. Rollins
*Attorney, Agent, or Firm*—Hamilton, Brook, Smith & Reynolds

[57] ABSTRACT

Recombination activating gene of mammalian origin (RAG-1), cDNA of RAG-1 of mammalian origin, mRNA expressed by RAG-1, the encoded recombinase and antibodies specific for the recombinase, as well as the use of the same for a diagnostic or therapeutic purpose.

5 Claims, 22 Drawing Sheets

EcoR I Digests

FIG. 6A

```
                                                                           Bal I
                                                                            |
GAGAGCAGAGAACACACTTTGCCTTCTCTCTTGGTATTGAGTAATATCAACCAAATTGCAGACATCTCAACACTTGGCCA    80
CTCTCGTCTCTTGTGTGAAACGGAAGAGAAACCATAACTCATTATAGTTGGTTTAACGTCTGTAGAGTTGTGAAACCGGT
                                                                              |
                                                                             75
 Kpn I
 Ban I                          Sty I
Bbv I Esp I  Asp718 Bgl I Bbv I
 |    |      |      |     |     |
GGCAGCCTGCTGAGCAAGGTACCTCAGCCAGCATGGCAGCCTCTCTTCCCACCCACCTTGGGACTCAGTTCTCGCCCAGAT   160
CCGTCGGACGACTCGTTCCATGGAGTCGGTCGTACCGTCGGAGAAAGGGTGGGTGGAACCCTGAGTCAAGAGCGGGTCTA
 |    |      |       |    |                                                   |
 82   89     98     107   116                                                 135
                                     BstY I
                             Hph I    |
                              |
GAAATTCAGCACCCACATATTAAATTTCAGAATGGAAATTTAAGCTGTTCCGGGTGAGATCCTTTGAAAAGACACCTGA   240
CTTTAAGTCGTGGGTGTATAATTTAAAGTCTTACCTTTAAATTCGACAAGGCCCACTGTAGGAAACTTTTCTGTGGACT
                                                                |       |
                                                               214     218  EcoN I
                                                                              |
AGAAGCTCAAAAGGAAAAGAAGGATTCCTTTGAGGGGAAACCCCTCTCTGAGCAATCTCCAGCAGTCCTGGACAAGGCTG   320
TCTTCGAGTTTTCCTTTTCTTCCTAAGGAAACTCCCCCTTTGGGAGAGACTCGTTAGAGGTCGTCAGGACCTGTTCCGAC
                                                                              |
                                                                             307
ATGGTCAGAAGCCAGTCCCAACTCAGCCATTGTAAAAGCCCACCCTAAGTTTTCAAAGAAATTTCACGACAACGAGAAA   400
TACCAGTCTTCGGTCAGGGTTGAGTCGGTAACAATTTCGGGTGGGATTCAAAGTTTCTTTAAAGTGCTGTTGCTCTTT
```

FIG. 6B

```
                                                                    HgiA I
                        Taq I                   EcoR I              Bsp1286 I
                         |                       |                   |  |      480
GCAAGAGAGGCAAAGCGATCCATCAAGGCCAACCTTCGACATCTCTGCCGCATCTGTGGGAATTCTTTAGAGCTGATGAGCA
CGTTCTCTCCGTTTCGCTAGGTAGTTCCGGTTGGAAGCTGTAGAGACGGCGTAGACACCCTTAAGAAAATCTCGACTACTCGT
                                                        |              |
         Sty I                                         457            476
    PflM I Ava II                                                     476
     |  |   |
EcoR V  Nco I                                        Stu I
 |      |                                            Sty I
 |      |                                            Avr II           560
                                                      | |
                                                      | |
CAACAGGAGATATCCAGTCCATGGTCCTGTGGATGGTAAAACCCTAGGCCTTTTACGAAAGAAGGAAAAGAGAGCTACTT
GTTGTCCTCTATAGGTCAGGTACCAGGACACCTACCATTTTGGGATCCGGAAAATGCTTTCTTCCTTTTCTCTCGATGAA
  |    |   |                                          |
489   494 499                                       523
             499                                    523              526

Ava II                               Taq I
    Gdi II         Sty I    BspM II      Cla I             HinC II    Taq I         640
     | |            |        | |          | |               |          |
CCTGGCCGGACCTCATTGCCAAGGTTTTCCGGATCGATGTGAAGGCAGAGTGTGACTGATCACCCCACTGAGTTCTGC
GGACCGGCCTGGAGTAACGGTTCCAAAAGGCCTAGCTACACTTCCGTCTCACAACTGACTAGTGGGGTGACTCAAGACG
 |              |             |              |                            |
563            579            588           593                          617
       568                                   594

Sty I
                                                                     PflM I
              Bsp1286 I                       Ava I                  Nco I         720
               |  |                             |                     |  |
CATAACTGCTGGAGCATCATGCACAGGAAGTTTAGCAGTGCCCATGTGAGGTTTACTTCCCGAGGAACGTGACCATGGA
GTATTGACGACCTCGTAGTACGTGTCCTTCAAATCGTCACACTCCAAATGAAGGGCTCCTTGCACTGGTACCT
                  |                            |                     |
                678                           700                   714
```

FIG. 6C

```
                                                                                    Bbv II               714
                                                                                     |                    714
        GTGGCACCCCACACCACCATCCTGTGACATCTGCAACACTGCCCGTCGGGACTCAAGAGGAAGAGTCTTCAGCCAAACT  800
Ban I   CACCGTGGGGTGTGTGGTAGGACACTGTAGACGTTGTGACGGGCAGCCCCTGAGTTCTCCTTCTCAGAAGTCGGTTTGA
 |
 723
                                                                                                  786
                                                                                                   Sac I
                                                                                                   HgiA I
                                                                                                   Bsp1286 I
                                                                                                   Ban II
        TGCAGCTCAGCAAAAACTGTCTTGACCAAGCAAGACAAGCCCGTCAGCGCAAGAGAAGAGCTCAGGCAAGG         880
Esp I   ACGTCGAGTCGTTTTTGACAGAACTGGTTCGTTCGTTCGGGCAGTCGCGTTCTCTTCTCGAGTCCGTTCC
 |                                                                              867
Bbv I                                                                           867
 |                                                                              867
 802                                                                            867
 805

BspH I              Pst I
                             |                    |
        ATCAGCAGCAAGGATGTCATGAAGAAGATCGCCAACTGCAGTAAGATACATCTTAGTACCAAGCTCCTTGCAGTGACTT  960
Bbv I   TAGTCGTCGTTCCTACAGTACTTCTTCTAGCGGTTGACGTCATTCTATGTAGAATCATGGTTCGAGGAACGTCACCTGAA
 |                                                            916
 885
 897

BstY I
                                Dra III  Bgl II  Xmn I
        CCCAGAGCACTTTGTGAAATCCATCTCCTGCCAGATCTGAACACATTCTGGCTGACCCTGTGGAGACCAACTGTAAGC  1040
HgiA I  GGGTCTCGTGAAACACTTTAGGTAGAGGACGGTCTAGACACTTGTGTAAGACCGACTGGGACACCTCTGGTTGACATTCG
Bsp1286 I
 |                            1001
 965                    993
 965                    993
 968
```

FIG. 6D

```
                Bsm I                          Bbv I                      EcoR V
                 |                              |                            |
ATGTCTTTTGCCGGGTCTGCATTCTCAGATGCCTCAAAGTCTCATGGGCAGCTATTGTCCCTCTTGCCGATATCCATGCTTC  1120
TACAGAAAACGGCCCAGACGTAAGAGTCTACGGAGTTTCAGTACCCGTCGATAACAGGGAGAACGGCTATAGGTACGAAG
                                    |          . 1086           .
                                   Hga I      EcoR I            Hph I
                                                 |                |
                                               1059             1107

CCTACTGACCTGGAGAGTCCAGTGAAGTCCTTCTGAATTCCCTGATGGTGAAATGTCCAGCAAAAGAGTG           1200
GGATGACTGGACCTCTCAGGTCACTTCAGGAAGACTTAAGGGACTACCACTTTACAGGTCGTTTTCTCAC
                                         |                       |
                                       1158                     1177
                                      1165
                                                                                 Ase I
                                                                                HgiA I
                                                                               Bsp1286 I
                 Hph I                                                           ApaL I
                  |                                                               |
CAATGAGGAGGTCAGTTTGGAAAAAATATAATCACCACATCTCAAGTCACAAGGAATCAAAAGAGATTTTTGTGCACATTA  1280
GTTACTCCTCCAGTCAAACCTTTTTTATATTAGTGGTGTAGAGTTCAGTGTTCCTTAGTTTTCTAAAAACACGTGTAAT
               |                                                                  |
             1231                                                               1271
                                                                                1271
                                                                                1271
                                                                                1277

Sac I                           Sac I
                                        HgiA I                          HgiA I
                                       Bsp1286 I                       Bsp1286 I
                                         Ban II          Cfr10 I        Ban II    Bbv I
                                           |                |             |         |
ATAAAGGGGCGCCCCGGCCGCCCAACATCTTCTGTCGCTGACTGCGGAGCTCAGAAGCACCGGCTGCTGAGGGAGCTCAAGCTG  1360
TATTTCCCCGCGGGGCCGGCGGGTTGTAGAAGACAGCTGACTGAGCCTCTCGAGTCTTCGTGGCCGACTCCCTCGAGTTCGAC
|                                             |             |             |        |
1290                                         1326          1338          1349      1357
1290                                         1326                        1349
 |                                           1326                        1349
Nae I                                        1326                        1349
Cfr10 I
```

FIG. 6E

```
CAAGTCAAAGCCTTTGCTGACAAAGAAGAAGGTGGAGATGTGAAGTCCGTGTGCATGACCTTGTTCCTGCTGGCTCTGAG    1440
GTTCAGTTTCGGAAACGACTGTTTCTTCTTCCACCTCTACACTTCCAGGCACACGTACTGGAACAAGGACGACCGAGACTC
          |                                      Bsp1286 I
     HgiA I                                      Ban II  Pst I  Bbv I
     Bsp1286 I                                                 Pvu II

GGCGAGGAATGAGCACAGCAAGCTGATGAGCTGGAGGCCATCATGCAGGGAAAGGGCTCTGGCCTGCAGCCAGCTGTTT    1520

CCGCTCCTTACTCGTCCGTTCGACTACTCGACCTCCGTAGTACGTCCCTTTCCCGAGACCGGACGTCGGTCGACAAA
                                                           |     |    |
                                                         1495   1505  1512
                                                         1495   1507
                             Pst I
                             Bbv I
     Bal I   HinC II         Pvu II

GCTTGGCCATCCGTGTCAACACCTTCCTCAGCTGCAGTCAGTACCACAAGATGTACAGGACTGTGAAAGCCATCACAGGG    1600
CGAACCGGTAGGCACAGTTGTGGAAGGAGTCGACGTCAGTCATGGTGTTCTACATGTCCTGACACTTTCGGTAGTGTCCC
                                 Sph I
       |            |            1551
     1524         1535           1552
                               Bsm I

AGACAGATTTTCAGCCTTTGCATGCCCTTCGGAATGCTGAGAAGGTACTTCTGCCAGGCTACCACCACTTTGAGTGGCA    1680
TCTGTCTAAAAGTCGGAAACGTACGGGAAGCCTTACGACTCTTCCATGAAGACGGTCCGATGGTGGTGAAACTCACCGT
                                                                          |
                |               |                                       Bbv I
              1621            1633                                      1678
            Bbv II
                |
              1699

GCCACCTCTGAAGAATGTCTTCCAGCACTGATGTTGGCATTATTGATGGGCTGTCTGGACTATCATCCTCTGTGATG    1760
CGGTGGAGACTTCTTACACAGAAGGTCGTGACTACAACCGTAATAACTACCCGACAGACCTGATAGTAGGAGACACCTAC
```

FIG. 6F

```
                                                            Bbv II
                                                            |
ATTACCCCAGTGGACACCATTGCAAAGAGAGTTCCGCTATGATTCAGCTTTGGTGTCTGCTTTGATGGACATGGAAGAAGAC   1840
TAATGGGTCACCTGTGGTAACGTTTCTCCAAGGCGATACTAAGTCGAAACCACAGACGAAACTACCTTCTTCTG
       .          .          .          .          .          .          .
                                                                           1835

Hph I                                                   1920
                          |
ATCTTGGAAGGCATGAGATCCCAAGACCTTGATGATTACCTGAATGGCCCCTTCACTGTGGTGAAGGAGTCTTGTGA
TAGAACCTTCCGTACTCTAGGGTTCTGGAACTACTAATGGACTTACCGGGGAAGTGACACCACTTCCTCAGAACACT
       .          .          .          .          .          .          .
                                                                                 BspH I
                                                                                 |
                                                                       1903

2000
TGGAATGGGAGACGTGAGTGAGAAGCATGGGAGTGGCCTGTAGTTCCAGAAAAGGCAGTCCGTTTTCATTCACAATCA
ACCTTACCCTCTGCACTCACTCTTCGTACCCTCACCCGGACATCAAGGTCTTTTCCGTCAGGCAAAAAGTAAGTGTTAGT
       .          .          .          .          .          .          .
                                                                           1998

2080
TGAAAATTACTATTGCCCACAGCTCTCAGAATGTGAAAGTATTTGAAGAAGCCAAACCTAACTCTGAACTGTTGCAAG
ACTTTTAATGATAACGGGTGTCGAGAGTCTTACACTTTCATAAACTTCTTCGGTTTGATTGAGACTTGACACAACGTTC
       .          .          .          .          .          .          .

Hga I
                                  |
CCATTGTGCCTTATGCTGGCAGATGAGTCTGACCACGAGACGCTGACCTGCCATCCTGAGTCCTCTCATTGCTGAGAGGA   2160
GGTAACACGGAATACGACCGTCTACTCAGACTGGTGCTGCGACTGACGGTAGGACTCAGAGAGTAACGACTCTCCCT
       .          .          .          .          .          .          .
                                           2119
```

FIG. 6G

```
                    Bsm I    BspM II                          Cfr10 I
                     |         |                               Ban I
          Ase I      |         |                              Bsp1286 I
           |         |         |                                |
           ·         ·         ·         ·         ·         · ||        ·
GGCCATGAAGAGCAGTGAATTAATGCTTGAGCTGGGAGGCATTCTCCGGACTTTCAAGTTCATCTTCAGGGGCACCGGCT    2240
CCGGTACTTCTCGTCACTTAATTACGAACTCGACCCTCCGTAAGAGGCCTGAAAGTTCAAGTAGAAGTCCCCGTGGCCGA
           |                             |                   || |
         2179                           2205                2230 |
                                                              2231
                                                                 2234

Taq I
          Xho I
          PaeR7 I                                  Acc I                  BstX I
          Ava I                                     |                       |
     Stu I ||                                       |                       |
      |  |||        ·         ·         ·         · |        ·         ·   |    ·
ATGATGAAAAACTTGTGCGGGAAGTGTGGGAAGGCCTCGAGGCTTCTGCGGCTCTACATTTGTACTCTTTGTGATGCCACC    2320
TACTACTTTTTGAACACGCCCTTCACCTTCCGGAGCTCCGAAGACGCCGAGATGTAAACATGAGAAACACTACGGTGG
      | |||                                         |                      |
    2269 |||                                      2291                   2316
        2273
        2273
        2273
        2274
          Bbv II
           |
           ·         ·         ·         ·         ·         ·         ·        ·
CGTCTGAAGCCTCTGAAAATCTTGTCTTCCACTCTATAACCAGAAGCCATGCTGAGAACCTGGAACGTTATGAGGTCTG    2400
GCAGACTTCGGAGAGTTTTAGAACAGAAGGTGAGATATTGGTCTTCGGTACGACTCTTGGACCTTGCAATACTCCAGAC
                           |
                         2345
```

FIG. 6H

```
                                    Hph I
                                     |
GCGTTCCAACCCTTACCATGAGTCTGTGGAAGAACTGCGGGATCGGGTGAAAGGGGTCTCAGCTAAACCTTTCATTGAGA    2480
CGCAAGGTTGGGAATGGTACTCAGACACCTTCTTGACGCCCTAGCCCACTTTCCCCAGAGTCGATTGGAAAGTAACTCT
                                                   .
                                      .           BstY I
                                    2446          Bgl II
                              Pvu II                |
                              Bbv II              . .
                                |  |             2538
                                .  .             2538
CAGTCCCTTCCATAGATGCACTCCACTGTGACATTGGCAATGCAGCTGAGTTCTACAAGATCTTCCAGCTAGAGATAGG    2560
GTCAGGGAAGGTATCTACGTGAGGTGACACTGTAACCGTTACGTCGACTCAAGATGTTCTAGAAGGTCGATCTCTATCCC
                                                              BspM II
                                                                |
                                                                .
                                                              2631
GAAGTGTATAAGAATCCAATGCTTCCAAAGAGGAAAGAAAAGGTGGCAGGCCACACTGACAAGCATCTCCGAAGAA    2640
CTTCACATATTCTTAGGGTTACGAAGGTTTCTCCTTTCCACCGTCCGGTGACCTGTTCGTAGAGGCCTTCTT
                                BspH I
                                  |
                                  .
                                2658
GATGAACCTCAAACCTCAAATCATGAGGATGAATGGCAACTTTGCCAGGAAGCTCATGACCAAAGAGACTGTGGATGCAGTTT    2720
CTACTTGGAGTTTGGAGTTTAGTACTCCTACTTACCGTTGAAACGGTCCTTCGAGTACTGGTTTCTCTGACACCTACGTCAAA
                                             .     .
                                           2691
                                           BstY I
                                             |
                                             .
                                           2770
GTGAGTTAATTCTTCCGAGGAGAGGCACGAGGCTCTGAGGAGCTGATGGATCTTTACCTGAAGATGAAACCAGTATGG    2800
CACTCAATTAAGAAGGCTCCTCTCCGTGCTCCGAGACTCCTCGACTACCTAGAAATGGACTTCTACTTTGGTCATACC
```

FIG. 6I

```
                                                                    Sac I
                                                                    HgiA I
                                                                    Bsp1286 I
                                                                    Ban II
                                                        Esp I
      Bsp1286 I                                           |
        |                                                 |
CGATCATCATGATGCCCTGCTAAAGAGTGCCCAGAATCCCTGCCAGTACAGTTCAATTCACAGCGTTTGCTGAGCTCCT   2880
GCTAGTAGTACGGGACGATTTCTCACGGGTCTTAGGGAGACGGTCATGTCAAGTTAAGTGTCGCAAAACGACTCGAGGA
        |                                                       |    2870
        2824                                                    2873
                                                                 2873
                                                                 2873
                                                                 2873

Hph I
TTCTACGAAGTTCAAGTATAGGGTATGAGGGAAAAATCACCAATTATTTCACAAAACCCTGCCCATGTTCCTGAAATTA   2960
AAGATGCTTCAAGTTCATATCCATACTCCCTTTTTAGTGGTTAATAAAGTGTTTGGACGGGTACAAGGACTTTAAT
                                        |
                                        2916

BspM II
                                                                      |
TTGAGAGGGATGGCTCCATTGGGCATGGCCAAGTGAGGGAAATGAGTCTGGTAACAAACTGTTTAGGCGCTTCCGAAA   3040
AACTCTCCCTACCGAGGTAACCCCGTACCCGTTCACTCCGTTCACTCCCTTTACTCAGACCATTGTTTGACAAATCCGCGAAGGCCTTT
                                                                     |
                                                                     3033

Bsm I
  |
ATGAATGCCAGCAGTCCAAATGCTATGAGATGGAAGATGTCCTGAAACACCACTGTTGTACACCTCCAAATACCTCCA   3120
TACTTACGGTCGTCGTCAGGTTTACGATACTCTACCTTCTACAGGACTTTGTGGTGACCAACATGTGGAGGTTATGGAGGT
  |
  3043
```

FIG. 6J

```
         Bsm I   Nsi I                    Bsu36 I       HinD III        Ava II
          -      -                         -             -       EcoO109 I
                                                                  -
GAAGTTTATGAATGCTCATAATGCATTAAAAACCCTCTGGGTTTACCATGAACCCTCAGGCAAGCTTAGGGACCCATTAG  3200
CTTCAAATACTTACGAGTATTACGTAATTTTTGGAGACCCAAATGGTACTTGGGAGTCCGTTCGAATCCCCTGGGTAATC
               -              -                 -          -       -
             3130            3141              3173        3181    3189
                                                                    3190

GCATAGAGGACTCTCTGGAAAGCCAAGATTCAATGGAATTTAAGTAGGGCAACCACTTATGAGTTGGTTTTTGCAATTG  3280

Hph I   PflM I
                                                -       -
CGTATCTCCTGAGAGACCCTTTCGGTTCCTTCTAAGTTACCTTAAAATTCATCCCGTTGGTGAATACTCAACCAAAAACGTTAAC

AGTTTCCCTCTGGGTTGCATTGAGGGCTTCTCCTAGCACCCTTTACTGCTGTGTATGGGGCTTCACCATCCAAGAGGTGG  3360
TCAAAGGGAGACCCAACGTAACTCCCGAAGAGGATCGTGGGAAATGACGACACATACCCCGAAGTGGTAGGTTCTCCACC
                                                               -       -
                                                             3343     3350

TAGGTTGGAGTAAGATGCTACAGATGCTCTCAAGTCAGGAATAGAAACTGATGAGCTGATTGCTTGAGGCTTTAGTGAG  3440
ATCCAACCTCATTCTACGATGTCTACGAGAGTTCAGTCCTTATCTTTGACTACTCGACTAACGAACTCCGAAAATCACTC
                                                        Pst I   Ava II
                                                         -       -
TTCCGAAAAGCAACAGGAAAAATCAGTTATCTGAAAGCTCAGTAACTCAGAACAGGAGTAACTGCAGGGACCAGAGATG  3520
AAGGCTTTTCGTTGTCCTTTTTAGTCAATAGACTTTCGAGTCATTGAGTCTTGTCCTCATTGAGTCTTGACGTCCCTGGTCTCTAC
                                                                -       -
                                                              3502    3509
```

FIG. 6K

```
BstY I
Bgl II                          Sty I                    Bgl I      PflM I
 |                               |                        |          |
AGCAAAGATCTGTGTGTGTTGGGGAGCTGTCATGTAAATCAAAGCCAAGGTTGTCAAAGAACAGCCAGTGAGGCCAGAAA    3600
TCGTTTCTAGACACACACAACCCCTCGACAGTACATTTAGTTTCGGTTCCAACAGTTTCTTGTCGGTCACTCCGGTCTTT
                                    |              |          |
                                   3526           3565       3584    3594
                                   3526

TTGGTCTTGTGGTTTCATTTTTTCCCCCTGATTGATTATATTTGTATTGAGATATGATAAGTGCCTTCTATTCAT        3680
AACCAGAACACCAAAAGTAAAAAAAGGGGGAACTAACTAATATAAACATAACTATACTATTCACGGAAGATAAGTA
                                                                Dra I
                                                                 |

TTTTGAATAATTCTTCATTTTTATAATTTTACATATCTTGGCTTGCTATATAAGATTCAAAAGAGCTTTTTAAATTTTC   3760
AAAACTTATTAAGAAGTAATAAAATATTAAAATGTATAGAACCGAACGATATATTCTAAGTTTTCTCGAAAAATTTAAAAG
                                                                         |
                                                                        3749

HgiA I  Nsl I
             Bsp1286 I
              |       |
TAATAATATCTTACATTTGTACAGCATGATGACCTTTACAAAGTGCTCTCAATGCATTACCATTCGTTATATAAATAT   3840
ATTATTATAGAATGTAAACATGTCGTACTACTGGAAATGTTCACGAGAGTTACGTAAATGGGTAAGCAATATATTATA
              |       |
             3803    3812
             3803
             Dra I
              |
             3883

GTTACATCAGGACAACTTTGAGAAAATCAGTCCTTTTTAATTATGTATCTATTGTAACCTTCAGAGTTTAGG          3920
CAATGTAGTCCTGTTGAAACTCTTTTAGTCAGGAAAAATTAATACATAGATAACATTGGAAGTCTCAAATCC
                                                 |
                                                3883

AGGTCATCTGCTGTCATGGATTTTTCAATAATGAATTAGAATACACCTGTTAGCTACAGTTAGTTATTAAATCTTCTGA   4000
TCCAGTAGACGACAGTACCTAAAAAGTTATTACTTAAATCTTATGTGGACAATCGATGTCAATCAATAATTTAGAAGACT
```

FIG. 6L

```
TAATATATGTTACTTAGCTATCAGAAGCCAAGTATGATTCTTTATTTTACTTTTCATTTCAAGAAATTTAGAGTTTC   4080
ATTATATATACAAATGAATCGATAGTCTTCGGTTCATCATACTAAGAAAATGAAAAAGTAAAGTTCTTTAAATCTCAAAG
                  Bgl I
                    |—|
                    4112
CAAATTAGAGCTTCTGCATACAGTCTTAAAGCCACAGAGGCTTGTAAAAAATATAGGTTAGCTTGATGTCTAAAAATATA   4160
GTTAAATCTCGAAGACGTATGTCAGAATTTCGGTGTCTCCGAACATTTTTATATCCAATCGAACTACAGATTTTTATAT

TTTCATGTCTTACTGAAACATTTTGCCAGACTTTCTCCAAATGAAACCTGAATCAATTTTCTAAATCTAGGTTTCATAG   4240
AAAGTACAGAATGACTTTGTAAAACGGTCTGAAACGGTTACTTTGGACTTAGTTAAAAGATTTAGATCCAAAGTATC
                                                    Bcl I
                                                     |—|
                                                     4277
AGTCCCTCCTCCTCTGCAATGTGTTATTCTTCTATAATGATCAGTTTACTTTCAGTGGATTCAGAATTGTGTAGCAGGATA   4320
TCAGGAGAGGAGACGTTACACAATATTACTAGTCAAATGAAAGTCACCTAAGTCTTAACACATCGTCCTAT

ACCTTGTATTTTCCATCCGCTAAGTTTAGATGGAGTCCAAACGGCCAGTACAGCAGAAGAGTTAACATTACACACTGCTT   4400
TGGAACATAAAAAGGTAGGCGATTCAAATCTACCTCAGTTTGCGTCGTCTTCCAATTGTAAATGTCACGAA
                                                           Hpa I
                                                           HincII
                                                            |—|
                                                            4380
                                                            4380
TTTACCACTGTGGAATGTTTCACACTCATTTTCCTTACAACAATTCTGAGGAGTAGTGTGTTATTATCTCCATTG   4480
AAATGGTGACACCTTACAAAAGTGTGAGTAAAAGGAATGTGTTAAGACTCCTCATCCACAACAATAATAGAGGTAAAC
Xmn I                                              PflM I
 |—|                                                |—|
 4413                                               4474
```

FIG. 6M

```
ATGGGGGTTTAATGATTGCTCAAAGTCATTTAGGGGTAATAAATACTTGGCTTGGAAATTTAACACAGTCCTTTGTCT    4560
TACCCCCAAATTACTAACGAGTTTCAGTAAACCCCATTATTTATGAACCGAACCTTTAAATTGTGTCAGGAAAACAGA
                            |
                           Ase I

CCAAAGCCCCTCTCTTCCACCACAAATTAATCACTATGTTTATAAGGTAGTATCAGAATTTTTTAGGATTCACAACT    4640
GGTTTCGGGGAGAAGAAGGTGGTGTTAATTAGTGATACAAATATTCCATCATAGTCTTAAAAAAATCCTAAGTGTTGA
                        |                                    Hg1A I
                      4588                              Dra I  Bsp1286 I

AATCACTATAGCACACATGACCTTGGGATTACATTTTTATGGGCAGGGTAAGCGGCTTTAAATCATTTGTGCCTCTGG    4720
TTAGTGATATCGTGTGTACTGGAACCCTAATGTAAAAATACCCGTCCCCATTCGCCGAAAATTAGTAAACACACGAGACC
          |                    |               |                     |
        Sty I               EcoO109 I                                4712
                            Bsp1286 I                                4712
                            Ban II
                            Apa I
         |                  EcoO109 I
       4659                     ||
                              4757
                              4758
                              4758                              BstX I
                              4758
                              4758

CTCTTTTGATAGAAGAAAGCAACACAAAGCTCCAAAGGGCCCCCCTAACCCTCTTGTGCTCCAGTTATTTGGAAACTAT    4800
GAGAAAACTATCTTCTTTCGTTGTGTTTCGAGGTTTCCCGGGGGATTGGGAGAACACCGAGGTCAATAAACCTTTGATA
                                                             |
                                                           4782
```

FIG. 6N

```
       Bsu36 I              PflM I
         |                    |
GATCTGCATCCTTAGGAATCTGGGATTTGCCAGTTGCTGGCAATGTAGAGCAGGCAGGCATGAATTTATATGCTAGTGAGTC  4880
CTAGACGTAGGAATCCTTAGACCCTAAACGGTCAACGACCGTTACATCTCGTCCGTACCTTAAAATATACGATCACTCAG
                  |
                 4810
                                                Bal I
                                                  |
ATAATGATATGTTAGTGTTAATTAGTTTTTCTTCCTTTGATTTTATTGGCCATAATTGCTACTCTTCATACACAGTATAT  4960
TATTACTATACAATCACAATTAATCAAAAGAAGGAAATCAAAACCGGTATTAACGATGAGAAGTATGTCATATA
         |                                      |
        4830                                  4927

CAAAGAGCTTGATAATTAGTGTCAAAAGTGCATCGGCGACATTATCTTTAATTGTATGTATTGGTGCTTCTTCAGGG     5040
GTTTCTCGAACTATTAATCAACAGTTTTCACGTAGCCGCTGTAATAACATAAACCACGAAGAAGTCCC

ATTGAACTCAGTATCTCTTCATTAAAAAACACAGCAGTTTCCCTTGCTTTTATATGCAGAATATCAAAGTCATTCTAAT   5120
TAACTTGAGTCATAGAAAGTAATTTTTGTCGTCAAAGGAACGAAAAATATACGTCTTATAGTTTCAGTAAAGATTA

TTAGTTGTCAAAAACATATACATATTTAACATTAGTTTTTTGAAAACTCTGGTTTGTTTTTTGAAATGAGTGGG        5200
AATCAACAGTTTTGTATATGTATAAATTGTAATCAAAAAAACTTTTGAGAACCAAAAACAAAAAACCTTTACTCACCC

CCACTAAGCCACACTTTCCCTTCCATCCTGCTTAATCCTTCCAGCATGTCTCTGCACTAATAAACAGCTAAATTCACATAA 5280
GGTGATTCGGTGTGAAGGGAAGTAGGACGAATTAGGACGTCGTACAGAGACGTGATTATTGTCGATTAAGTGTATT

TCATCCTATTTACTGAAGCATGGTCATGCTGGTTTATAGATTTTTACCCATTCTACTCTTTTTCTCTATTGGTGGCAC   5360
AGTAGGATAAATGACTTCGTACCAGTACGACCAAATATCTAAAAATGGTAAAGATGAGAAAAGAGATAACCACCGTG
```

FIG. 60

```
                                    Nsi I
                                    Bsm I
                                    | |
TGTAAATACTTTCCAGTATTAAATTATCCTTTTCTAACACTGTAGGAACTATTTGAATGCATGACTAAGAGCATGAT    5440
ACATTTATGAAAGGTCATAATTTAATAGGAAAAGATTGTGACATCCTTGATAAACTTACGTACACTGATTCTCGTACTA
                                                      | |
                                                      5416
                                                      5418

Pst I
                                                                    Bbv I
                                                                    | |
TTATAGCACAACCTTTCCAATAATCCCTTAATCAGATCACATTTTGATAAACCCTGGGAACATCTGGCTGCAGGAATTTC    5520
AATATCGTGTTGGAAAGGTTATTAGGGAATTAGTCTAGTGTAAAACTATTTGGGACCCTTGTAGACCGACGTCCTTAAAG
                                                                    | |
                                                                    5507
                                                                    5508

AATATGTAGAAACGCTGCCTATGGTTTTTGCCCTTACTGTTGAGACTGCAATATCCTAGACCCTAGTTTATACTAGAG    5600
TTATACATCTTTGCGACGGATACCAAAACGGGAATGACAACTCTGACTGTTATAGGATCTGGGATCAAAATATGATCTC
  |
Bbv I
  |
5534

Hph I       Taq I
                                                              |           |
TTTTATTTTAGCAATGCCTATTGCAAGTGCAATTATATACTCCAGGAAATTCACCACACTGAATCGAGCATTTGTGTG    5680
AAAATAAAATCGTTACGGATAACGTTCACGTTAATATATGAGGTCCTTTAAGTGGTGTGACTTAGCTCGTAAACACAC
                                                              |           |
                                                              5653        5666

TGTATGTGTGAAGTATATCGGGACTTCAGAAGTGCAATGTATTTTCTCCTGTGAAACCTGAATCTACAAGTTTCTGC    5760
ACATACACACTTCATATAGCCCTGAAGTCTTCACGTTACATAAAAGAGGACACTTTGACTTAGATGTTCAAAGACG
```

FIG. 6P

```
                Ava II                                                     Sty I
                 |                                                          |
CAAGCCACTCAGGTGCATTGCAGGGACCAGTGATAATGGCTGATGAAATTGTGATGATTGGTCAGTGAGTCAAAAGGAGC  5840
GTTCGGTGAGTCCACGTAACGTCCCTGGTCACTATTACCGACTACTTTAACTACTAACCAGTCACTCAGTTTTCCTCG
         .         .         .         .         .         .         .         .
                                                                       5840
         Ase I                                     Hph I
          |                                         |
CTTGGGATTAATAACATGCACTGAGAAGCAAGAGGAGGAGAAAAAGATGTCTTTTCTTCCAGGTGAACTGGAATTTAG  5920
GAACCCTAATTATTGTACGTGACTCTTCGTTCCTCCTCCTCTTTTTCTACAGAAAAGAAGTCCACTTGACCTTAAATC
         .         .         .         .         .         .         .         .
     5847                                       5904
TTTTGCCTCAGATTTTTTCCCACAAGATACAGAAGAAGATAAAGATTTTTTGGTTGAGAGTGTGGGTCTTGCATTACA  6000
AAAACGGAGTCTAAAAAAGGGTGTTCTATGTCTTCTTCTATTTCTAAAAAACCAACTCTCACACCCAGAACGTAATGT
         .         .         .         .         .         .         .         .
                                                                   PflM I
                                                                    |
TCAAACAGAGTTCAAATTCCACACAGATAAGAGGCCAGGATATATAAGCGCCCAGTGGTAGTTGGGAGGAATAACCATTAT  6080
AGTTTGTCTCAAGTTTAAGGTGTGTCTATTCTCCGTCCTATATATTCGCGGTCACCATCAACCCTCCTTATTGGTAATA
         .         .         .         .         .         .         .         .
                                                                  6074
  BspM I             Bbv II
     |                 |
TTGGATGCAGGTGGTTTTGATTGCAAATATGTGTGTCTTCAGTGATTGTATGACAGATGATGTATTCTTTTGATGTT  6160
AACCTACGTCCACCAAAAACTAACGTTTATACACACAGAAGTCACTAACATACTGTCTACTACATAAGAAAACTACAA
         .         .         .         .         .         .         .         .
    6087                                  6118
AAAAGATTTAAGTAAGAGTAGATACATTGTACCCATTTTACATTTCTTATTTTAACTACAGTAATCTACATAAATATA  6240
TTTTCTAAATTCATTCTCATCTATGTAACATGGGTAAAATGTAAAAATGAATAAAATTGATGTCATTAGAGTATTATAT
         .         .         .         .         .         .         .         .
```

FIG. 6Q

```
                    Hph I
                     |
CCTCAGAAATCATTTTGGTGATTATTTTGTTTTGTAGAATTGCACTTCAGTTTATTTCTTACAAATAACCTTACAT    6320
GGAGTCTTTAGTAAAACCACTAATAAAAACAAACATCTTAACGTGAAGTCAAATAAAAGAATGTTTATTGGAATGTA
                    •     6258
                                                             Kpn I
                                                             Ban I
                                                             Asp718
                                                              |
TTTGTTTAATGGCTTCCAAGAGCCCTTTTTTTTTGTATTCAGAGAAAATTCAGGTACCAGGATGCAATGGATTTATTT    6400
AAACAAATTACCGAAGGTTCTCGGGAAAAAAACATAAAGTCTCTTTTAAGTCCATGGTCCTACGTTACCTAAATAAA
                                                              6375
                                                              6375
                                                              6375
 Ava II
 EcoO109 I                                                                  Ssp I
  | |                                                                        |
GATTCAGGGGACCCTGTATTTCCATGTCAAATGTTTCAAATAAAATGAGTTTCAATACTTTTTATATTTTAAT    6480
CTAAGTCCCCTGGACATAAAGGTACAGTTTACAAAGTTTATTTTACTTAAATATGAAAAATATAAAATTA
  ||                                                                        |
  6408                                                                      6478
  6409
```

RECOMBINATION ACTIVATING GENE (RAG-1)

DESCRIPTION

Funding

Work described herein was funded by the American Cancer Society (Grant No. IM-355T); The Life and Health Insurance Medical Research Fund; The Whitaker Health Sciences Fund; and The Johnson and Johnson/Health Sciences and Technology Fund.

Background

Assembly of immunoglobulin (Ig) heavy and light chain genes and of α and β chain genes of the T cell receptor occurs in developing lymphocytes by somatic recombination, in which widely separated gene segments are joined to form a complete variable region. The variable region is assembled from V (variable), J (joining) and, in some cases, D (diversity) gene segments in an ordered and highly regulated manner.

Complex mechanisms regulate V(D)J recombination and these mechanisms are still not well understood. It is known that recombinationally active gene segments are flanked by conserved DNA sequences, called joining sequences, which are composed of highly conserved heptamer and nonamer regions which are separated from each other by a spacer region. The spacer region's sequence is not conserved, but, in most cases, the region is 12 or 23 base pairs (bp) in length. Sakano, H. et al. *Nature*, 280:288-294 (1979); Max, E. E. et al., *Proc. Natl. Acad. Sci., U.S.A.*, 76:3450-3454 (1979); Early, P. et al., *Cell*,19:981-992 (1980); Sakano, H. et al. *Nature*, 290:562-565 (1981); Davis, M. M., *Annu. Rev. Immunol.*, 3:537-560 (1985). Gene segments flanked by joining signals with 12 bp spacers are joined only to gene segments flanked by joining signals with 23 bp spacers.

There are several additionaly layers of regulation superimposed on restrictions dictated by the joining signals. Developing B cells and T cells rearrange distinct gene segment families in a well-defined temporal order. In developing B cells, the heavy chain locus is rearranged before the light chain loci. Maki, R. et al., *Science*, 209:1366-1369 (1980); Perry, R. P. et al., *Proc. Natl. Acad. Sci., U.S.A.*, 78:247-251 (1981); Alt, F. et al., *Cell*, 27:381-390 (1981); Alt, F. et al., *EMBO J.*, 3:1209-1219 (1984); Reth, M. G. et al., *Nature*, 317:353-355 (1985). In developing T cells, the β chain locus is rearranged before the α chain locus. Raulet, D. H. et al., *Nature*, 314:103-107 (1985); Snodgrass, H. R. et al., *Nature*, 315:232-233 (1985); Samelson, L. E. et al., *Nature*, 315:765-768 (1985). Although different sets of genes are rearranged in developing B and T cells, exogenously introduced T cell receptor gene segments can be efficiently recombined in pre-B cells. This suggests that B and T cell lineages use the same recombination machinery. Yancopoulos, G. D. et al., *Cell*, 44:251-259 (1986).

Little is known about the enzymatic machinery that carries out V(D)J recombination. It is not known if the recombinase is one or several enzymes, some or all of which might be lymphoid-specific. Schatz, D. G. and D. Baltimore, *Cell*, 53:107-115 (1988). Activities expected to be associated with the recombinase include recognition of joining signals, cleavage of DNA at the juncture between joining signals and coding region gene segments and ligation of the cleaved ends. The mechanism of the molecular events involved in recombination is unknown. Lewin, B., *Genes III*, p. 650-653, John Wiley & Sons (1988). It would be helpful to know how recombination of variable region genes occurs because an understanding of the process would make it possible to correct defectes in immune system function and also enhance immune system activity.

SUMMARY OF THE INVENTION

The present invention relates to the isolation and cloning of the recombination activating gene (RAG-1); to genomic DNA of mammalian origin containing the RAG-1 gene and cDNA of mammalian origin of RAG-1; to the encoded RAG-1 product; and to uses of the gene and the encoded product. All or a portion of RAG-1 can be used for diagnostic or therapeutic purposes, such as to detect a genetic disease (e.g., an immune deficiency) and/or to treat an immunological defect or deficiency. In addition, RAG-1 can be used as a highly specific marker for typing and staging human lymphoid malignancies (e.g., lymphomas, leukemias). RAG-1 can be introduced into human hematopoietic cells to stimulate the growth and/or development of specific subsets of these cells. This may prove useful, for example, in treating individuals with Acquired Immunodeficiency Syndrome (AIDS), in whom introduction and expression of RAG-1 could stimulate growth and development of new CD4+T-cells and, thus, counter the major immunological defect in such individuals.

BRIEF DESCRIPTION OF THE DRAWINGS

FIG. 6 is a partial nucleotide sequence of human RAG-1, with a number of restriction enzyme sites indicated.

DETAILED DESCRIPTION OF THE INVENTION

The present invention relates to a gene of mammalian origin, referred to as recombination activating gene or RAG-1, which confers the ability to carry out V(D)J recombination on cells in which it is expressed. The RAG-1 gene product is thus a direct or indirect activator of V(D)J recombinase activity. The invention also refers to RAG-1 mRNA and to the RAG-1 encoded product. RAG-1 has been shown in pre-B and pre-T cells, as well as in all transfectants into which it has been introduced. This pattern of expression is that expected for the V(D)J recombinase and, therefore, RAG-1 appears to be a master controller of the development of the effector cells of the immune system. The RAG-1 cDNA has been shown to cross hybridize in many species, such as mouse, rabbit, dog, goat, horse and human, indicating that it is highly conserved across species. Human cDNA of the RAG-1 gene; mouse genomic DNA containing the RAG-1 gene; and mouse cDNA of the RAG-1 gene have been cloned, as described below.

Transfection of genomic DNA into NIH 3T3 fibroblast cells results in stable activation of V(D)J recombination in some recipients. The human and the mouse copies of RAG-1, isolated as described herein, have been shown to be capable of activating recombination in mouse 3T3 fibroblasts. Human and mouse RAG-1 have been shown to be expressed primarily, if not exclusively, as a 6.5 kilobase (kb) mRNA, in a highly cell-type and tissue-type specific manner. That is, it is detected in pre-B cells, pre-T cells and in RNA derived from murine fetal and adult thymus. It is also detected in NIH 3T3 cells that have been transfected with genomic DNA and are expressing V(D)J recombinase activity. It was not detected in fibroblasts, mature B-cells, myeloma cells, mature T-cells and a number of murine fetal and adult tissues. A partial nucleic acid sequence of RAG-1 has been determined, compared with sequence in available data banks (GENBANK, NBRF) and shown not to be the same as any other known nucleic acid sequence. Similarly, the amino acid sequence of the recombinase has been compared with sequences in available data banks (GENBANK, NBRF) and shown not to be the same as any other known protein.

The following is a description of the isolation and cloning of the RAG-1 gene, using a genomic transfection protocol which makes it possible to identify cells in which inversional rearrangements have occurred. This protocol was carried out twice, as described below.

Figure 1:
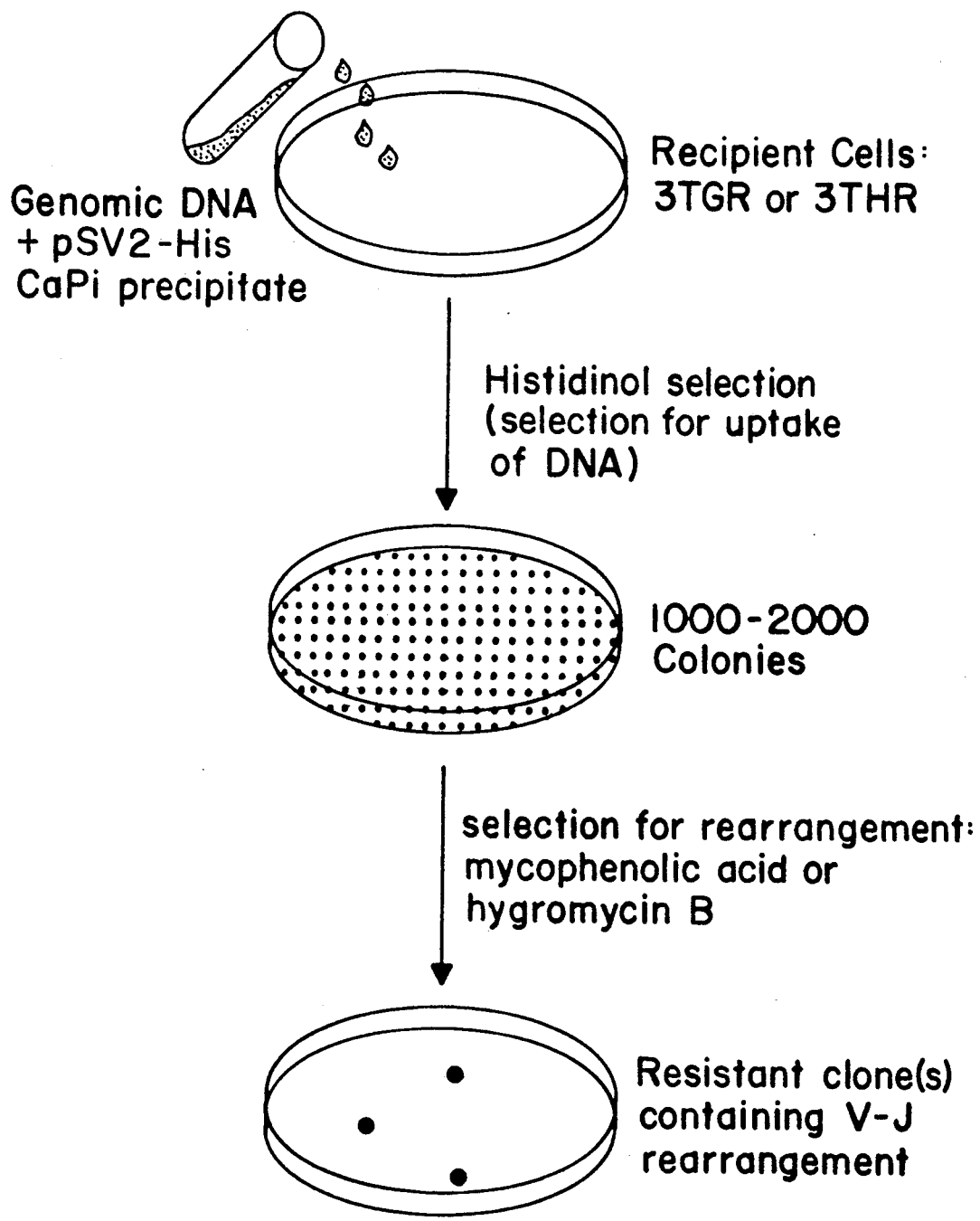
FIG. 1 is a schematic representation of the protocol for genomic transfection used to identify clones containing V-J rearrangement.

As shown in FIG. 1, NIH 3T3 cells without recombinase activity (3TGR) were transfected with a precipitate of calcium phosphate and DNA. Graham, G. L. and A. J. van der Eb, *Virology*, 52:456-467 (1973); Parker, B. A. and G. R. Stark, *J. Virol.*, 31:360-369 (1979). 3TGR is a 3T3 clone which contains two copies of the DGR provirus. pDGR is a retrovirus-based DNA substrate which incorporates germ line Ig variable region gene segments (Ig κ V and J segments) in opposite transcription orientation; a marker (xanthine-guanine phosphoribosyl-transferase (gpt) gene) that signals rearrangement of the Ig gene segments; and an independent marker (constitutively expressed neomycin (neo) gene) for selection of cells that have integrated the retrovirus. In pDGR, the gpt gene is positioned between the Ig gene segments and oriented so that the inversional rearrangements are selected. The gpt gene in pDGR lacks a eukaryotic promoter until inversional rearrangement occurs, which brings the gene under the control of the 5' LTR. As a result, the gpt gene is expressed, conferring mycophenolic acid resistance on cells. The presence of pDGR in 3TGR cells makes it possible to determine whether V-to-J rearrangements have occurred.

Figure 2:
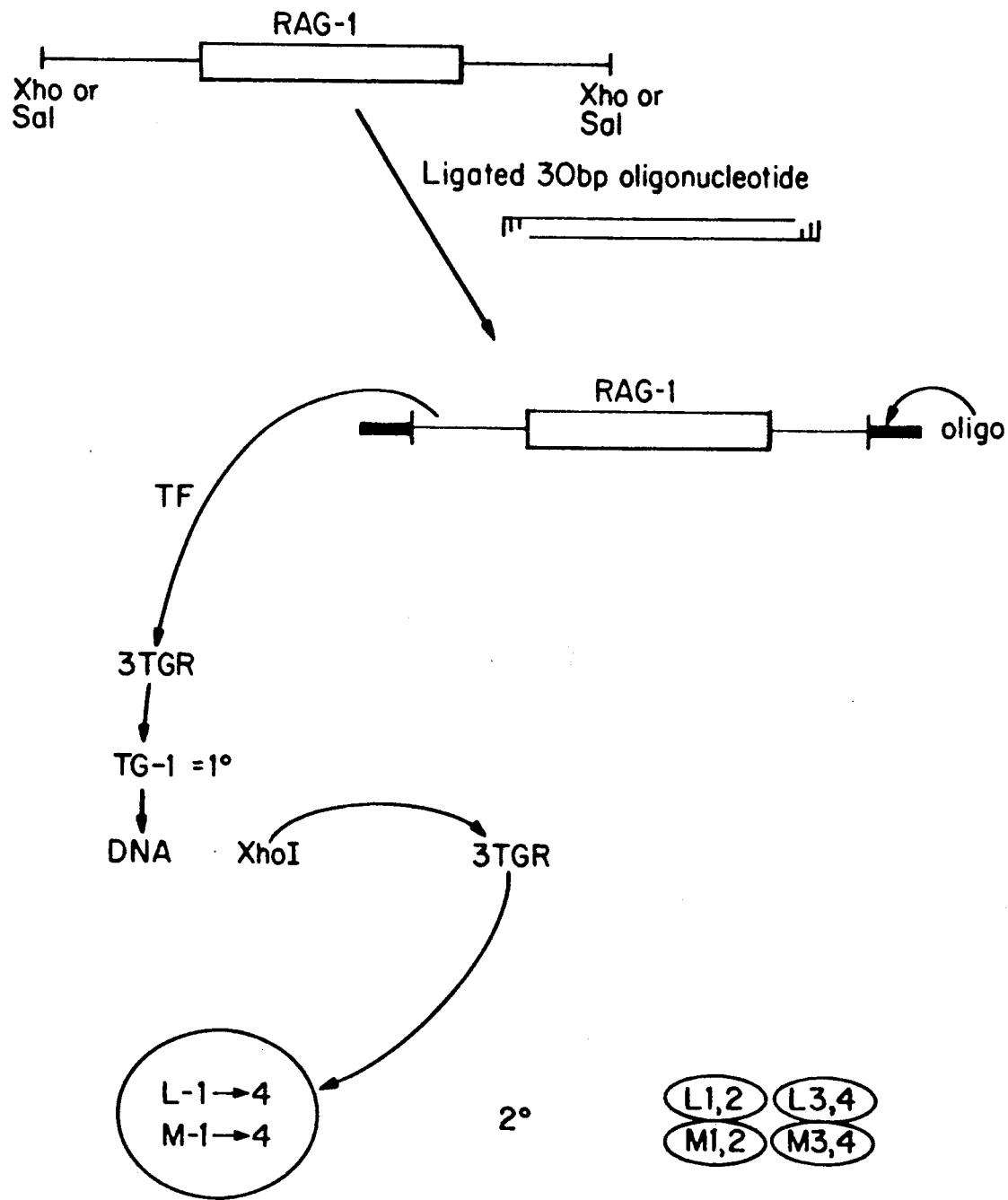
FIG. 2 is a schematic representation of screening of genomic DNA with a 30 bp oligonucleotide probe and selection of clones thought to contain RAG-1.

Genomic DNA from the secondary transfectant TRX1 was digested to completion with restriction enzymes XhoI and SalI. The resulting fragments were ligated to a 30 bp oligonucleotide having end sequences compatible with the ends of XhoI or SalI restriction fragments. As shown in FIG. 2, this produced a mixture containing DNA fragments which contained the desired RAG-1 gene ligated to the oligonucleotide and DNA fragments which did not contain RAG-1 ligated to the oligonucleotide. Production of TRX1 is described in the Exemplification.

The resulting ligation mixture was cotransfected into 3TGR with the cotransfectable marker plasmid pSV2-His, whose marker gene, histidinol dehydrogenase, confers resistance to histidinol. The resulting mixture (3TGR transfectants and untransfected 3TGR cells) was plated onto histidinol-containing medium. This resulted in growth of cells which took up the DNA (cotransfectants). A second selection step (cultivation in mycophenolic acid-containing medium) resulted in selection for pDGR, which is present in 3TGR cells (i.e., for rearrangement of DGR and expression of the gpt gene).

Figure 3:
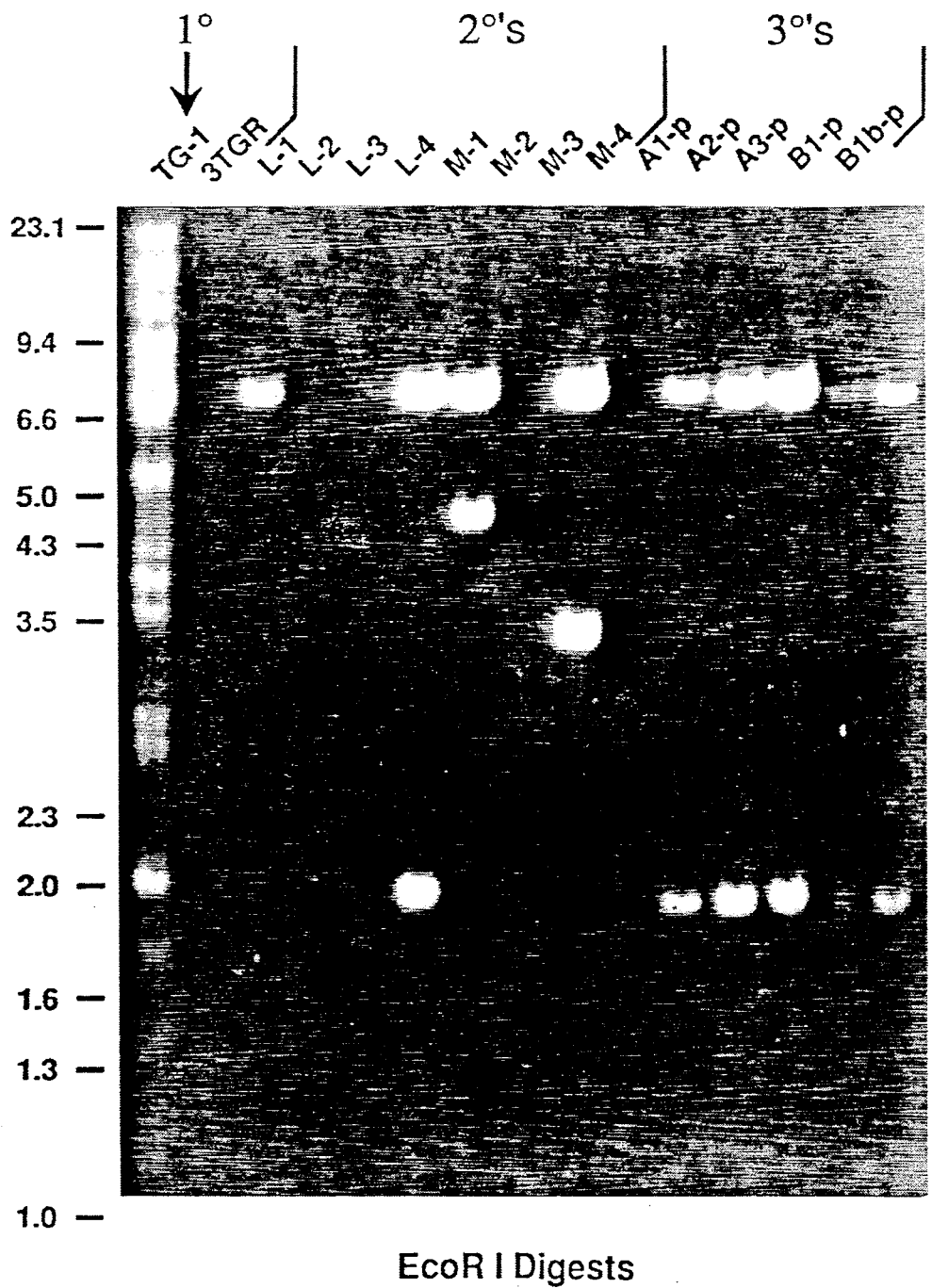
FIG. 3 is a photograph of a Southern blot showing results of oligonucleotide tagging of RAG-1.

As a result of this selection process, resistant clones containing V-J rearrangements were identified. One of these clones, designated TG-1, was used as the primary transfectant for cloning purposes. DNA from TG-1 and 3TGR was digested with EcoRI, fractionated on an agarose gel, and probed with the 30 bp oligonucleotide described previously. As shown in FIG. 3, no hybridization of the 3TGR DNA with the oligonucleotide probe occurred (lane 2). Many bands were produced, however, when TG-1 DNA was probed with the oligonucleotide. This was evidence of the presence of many fragments ligated to the oligonucleotide. However, it did not provide an indication of which bands, if any, represent fragments in which the oligonucleotide was in close proximity to RAG-1.

DNA from TG-1 was next cut with XhoI, as represented in FIG. 2, and transfected into 3TGR, as described previously. The same selection protocol (histidinol selection followed by mycophenolic acid selection) was carried out and resulted in identification of eight secondary transfectants, two from each of four separate plates of cells (i.e., from four independent transfection events). (The four sets of plates were as follows: L1, L2; L3, L4; M1, M2; and M3, M4). These transfectants were probed with the 30 bp oligonucleotide. As shown in FIG. 3, DNA from four transfectants (L-2, L-3, M-2, M-4) did not hybridize with the oligonucleotide, demonstrating that in these transfectants, RAG-1 was not linked to the oligonucleotide. As also shown in FIG. 3, DNA from the remaining four transfectants (L-1, L-4, M-1 and M-3) did hybridize to the oligonucleotide, with each of the four transfectants a 7.5 kb EcoRI fragment the hybridized to the oligonucleotide. This result strongly suggested that this 7.5 kb EcoRI fragment was closely linked to the RAG-1 gene. DNA from L-4 was also used to generate teritiary transfectants, further confirming this result.

Figure 4:
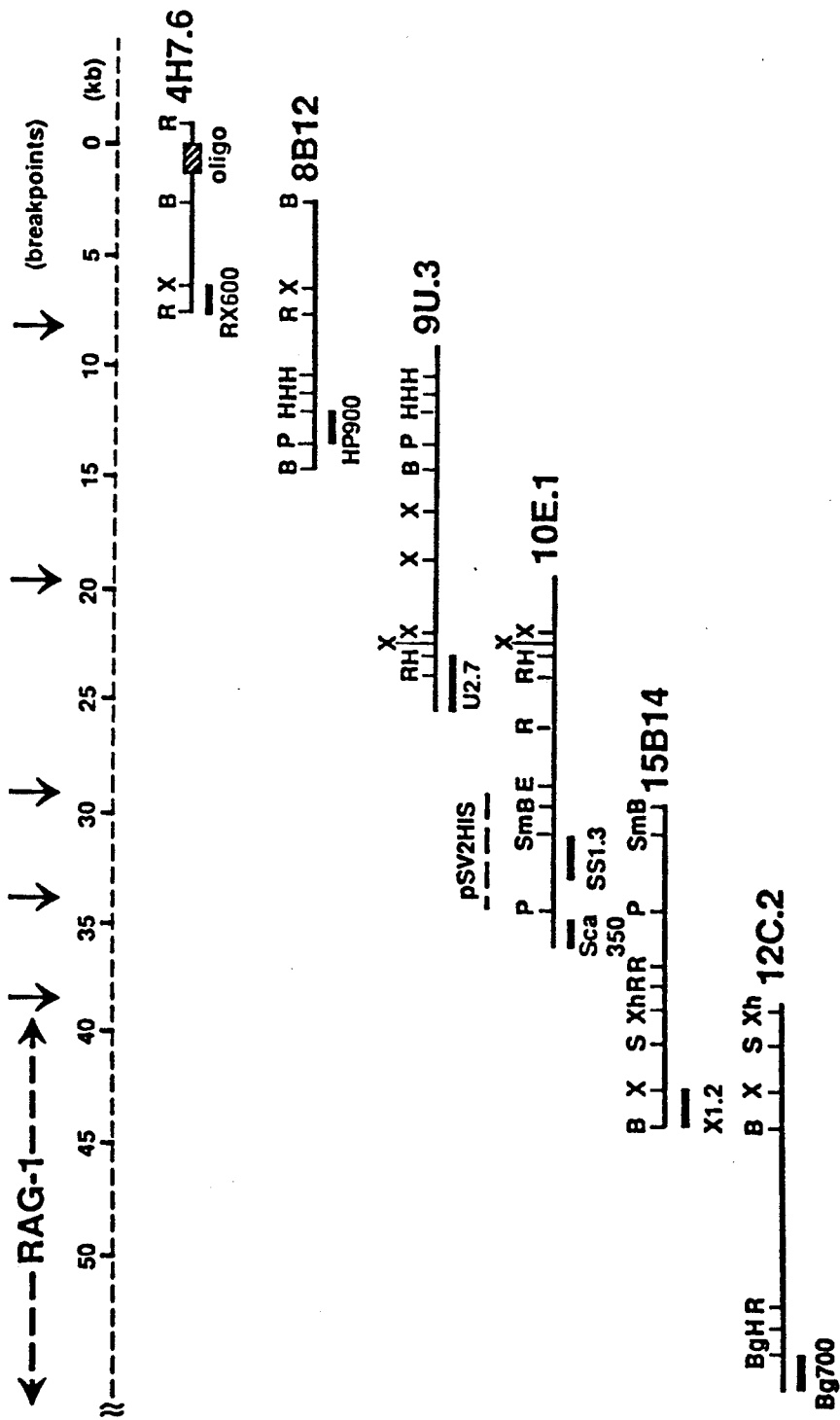
FIG. 4 is a schematic representation of the genomic walk toward RAG-1.
Figure 5:
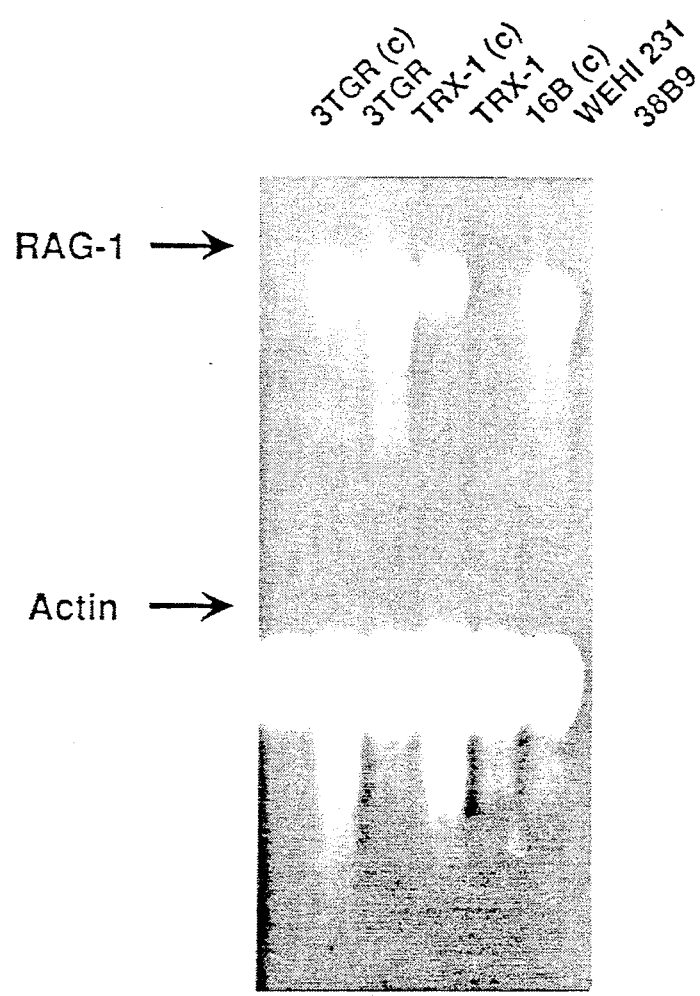
FIG. 5 is a photograph of a Northern blot of poly A+RNA derived form total cellular RNA or from cytoplasmic (c) RNA.

A genomic walk, using standard recombinant DNA methods, was carried out to locate RAG-1. The walk is represented schematically in FIG. 4 and, as indicated, began with the 7.5 kb EcoRI fragment, designated 4H7.6, which hybridized to the oligonucleotide. Probe RX600 was derived from 4H7.6 and was used to probe a genomic DNA library from which the next fragment, designated 8B12 in FIG. 4, was derived. This fragment gave rise to probe HP900, which in turn, was used to probe a new genomic DNA library and pull out a third clone (9U.3 in FIG. 4), which was the source of the next probe used. This procedure was repeated, each time with a new probe derived from the left-most region of the DNA insert of the clone pulled out by the preceding probe. The correct direction for the walk had initially been determined using Southern blots of a large panel of independent genomic transfectants. The walk continued approximately 55 kb (to the left) from fragment 4H7.6, until fragment Bg700 was obtained. When Bg700 was hybridized to Northern blots, mRNA with the properties and the expression pattern expected of RAG-1 (based on the fact that recombination occurs only in specific types of cells) was identified. As shown in FIG. 5, which is a Northern blot of poly A+RNA from total cellular RNA or from cytoplasmic (c) RNA, mRNA was identified in the genomic transfectants TRX-1 and 16B, and in 38B9 cells, which are pre B cells. It was shown not to be present in RNA 3TGR cells, which are known to have no recombinase activity, or in WEHI 231 cells, which are mature B cells, which also lack recombinase activity.

Bg700 was used to probe cDNA libraries, such as the human pre B cell library from the cell line NALM6. As a result, a clone, designated H36, containing RAG-1 was obtained. The H36 cDNA insert was suncloned into the eukaryotic expression vector pJ3 $\Omega$ and the resulting subclones have been tranfected into 3TGR cells to test the cDNA for biological activity. Such cells can be tested for V(D)J recombinase activity, as described previously. Activation of V(D)J recombinase activity in NIH 3T3 cells by expression of the human cDNA clone will prove the identity of the H36 cDNA. Human cDNA for RAG-1 cloned into pJ3 $\Omega$ at BamHI-CLaI sites has been deposited at the American Type Culture Collection (Rockville, Md.), according to the terms of the Budapest Treaty, under accession number 40617. 3TRG cells transfected with H36-pJ3 $\Omega$ have given rise to mycophenolic acid resistant clones, and these clones will be tested by Southern blot analysis to demonstrate the occurrence of recombination and, thus, the presence of recombinase activity and of RAG-1.

Using the same protocol, a clone designated 12C.2, which contains mouse genomic DNA containing the RAG-1 gene, has been obtained. The DNA insert of clone 12C.2 has been transfected into 3TGR cells, using a bacteriophage containing the DNA and standard techniques. The resulting mixture of 3TGR cells (some transfected with 12C.2 DNA and some not transfected with 12C.2 DNA) has been subjected to the two-step selection procedure described previously. Clones which are mycophenolic acid resistant have been identified. This suggests that RAG-1 activity is present in these clones. Verification of RAG-1 activity can be carried out using the Southern blot procedure described. Mouse cDNA of RAG-1 has also been cloned, using the same protocol.

All or a portion of RAG-1 can be used as a probe to identify similar sequences in additional species. As a result of the work described herein, it is now possible to study the genomic organization of RAG-1 and to determine the chromosomal location of RAG-1 in human and mouse, as well as to determine whether RAG-1 maps close to a known disease locus. It has been suggested, for example, that there is a relationship between severe combined immunodeficiency disease (SCID) and lack of recombinase activity. Ichihara and co-workers found that their observations concerning SCID-derived precursor B cell lines are in line with the hypothesis that the defect in the SCID patient studied is in the putative recombinase itself, resulting in the prevention of both T- and B-cell differentiation. Ichihara, Y. et al., *Immunogenetics*, 27:330–337, Springer-Verlag (1988). All or a portion of RAG-1 can be used in a diagnostic context to determine the presence or absence of such a disease, once the relationship has been established. In addition, RAG-1 may be useful as a highly specific marker for typing and staging human lymphoid malignancies, including lymphomas and leukemias. This is the case because RAG-1 is very specificaaly expressed only in pre-B and pre-T cells.

Introduction of all or a portion of RAG-1 or an equivalent nucleic acid sequence into hematopoietic cells might stimulate growth and/or development of specific subsets of these cells. This can be used to counter or compensate for immune system deficiencies, such as that known to occur in indivuduals with AIDS. Introduction and expression of RAG-1 might result in growth and development of new CD4+T-cells and, thus, help counter the major immunological deficiency encountered in AIDS. RAG-1 can be introduced into hematopoietic cells by means of an appropriate vector, such as by transfection or infection with a recombinant retroviral construct containing RAG-1 and sequences necessary for its expression.

RAG-1 DNA used for diagnostic or therapeutic purposes can be RAG-1 obtained by removal or isolation from a source in which it occurs in nature or can be produced using standard genetic engineering techniques, such as cloning or chemical or mechanical synthesis. RAG-1 DNA or an equivalent DNA sequence (i.e., DNA which is sufficiently similar in sequence to RAG-1 that it encodes a product exhibiting recombinase activity) can be used. It is also possible to introduce mRNA encoding RAG-1 into an individual for therapeutic purposes, using the same procedure as described for RAG-1.

Antibodies, either polyclonal or monoclonal, specific for the RAG-1-encoded product can be produced using known techniques. For example, RAG-1-encoded protein can be injected into an appropriate animal, such as a rabbit, in whom polyclonal antibodies will be produced. The polyclonal antibodies can be recovered by separation from blood obtained from the animal. Monoclonal antibodies specific for RAG-1 can be produced using hybridoma technology. RAG-1-specific antibodies can be used for diagnostic purposes, such as typing and staging human lymphoid malignancies, or for the analysis of the extent of expression of RAG-1 in various tissues.

EXEMPLIFICATION

Production of TRX1

Fibroblasts containing DGR were transfected with genomic DNA from the human B cell lyphoma line, Raji. Raji has the phenotype of a mature B cell and is likely to lack recombinase activity (by analogy with WEHI 231). It was chosen only as a convenient human DNA donor. The recipient of the transfection, 3TGR, was a 3T3 clone containing two copies of the DGR provirus, described above.

3TGR was cotransfected with Raji genomic DNA and the plasmid pSV2-His, whose marker gene, histidinol dehydrogenase, confers resistance to histidinol. Cells that had taken up DNA were selected in histidinol, and were then selected for rearrangement of DGR, and expression of the gpt gene, using mycophenolic acid. From a pool of approximately 1500 independent histidinol-resistant colonies, a single mycophenolic acid-resistant clone, TR-1, was obtained.

Gel transfer hybridization of BamHI-HindIII digested DNA from 3TGR and TR-1 revealed a new band in TR-1 that comigrated with the upper, major rearranged band in 38B9TK$^-$. To confirm that one copy of DGR in TR-1 had undergone a proper V-to-J rearrangement, the DGR proviruses of TR-1 were rescued by the method of cos cell fusion and the region containing the V-J junction was sequenced. Cepko, C.

L. et al., Cell, 37:1053–1062 (1984). This revealed a typical V-J junction with two nucleotides missing from each of the coding regions. No cells containing a rearranged provirus were observed in a control transfection using yeast genomic DNA and pSV2-His.

A second transfection of 3TGR was performed using TR-1 DNA as donor and pSV2-His. The secondary transfection was complicated by the fact that TR-1 contained a rearranged copy of DGR that could confer mycophenolic acid resistance directly on a recipient cell. To inactivate the rearranged copy of DGR, the TR-1 DNA to be transfected was first digested to completion with the enzyme XhoI. In the rearranged configuration of DGR, Xhol cuts between the gpt gene and the 5'LTR, separating the gene from its promoter and thereby inactivating it. Furthermore, XhoI cuts genomic DNA infrequently, which increased the likelihood that it would leave the gene or genes of interest intact.

Two independent secondary transfections of 3TGR with XhoI-digested TR-1 DNA yielded two mycophenolic acis-resistance colonies (TRX-1 and TRX-2) from one of the transfections. Gel transfer hybridization with DNA from TRZ-1 and TRX-2 demonstrated that each contained a BamHI-HindIII fragment that comigrated with the larger rearranged band from DGR-infected 38B9TK cells and with the rearranged band for TR-1. To show that this band was derived from rearrangement of a copy of DGR endogenous to the 3TGR recipient cells of the secondary transfection and not from the donor TR-1 DNA, the various DNAs were digested with BamHI and subjected to gel transfer hybridization. BamHI digestion gave fragments recognized by probe 1 that are cut once in the provirus and once in the flanking DNA, allowing the two proviruses in 3TGR to be recognized. In TRX-1 and TRX-2, one characteristic band was absent and a new BamHI fragment was evident. Because the bands in TRX-1 and TRX-2 were like those in TR-1 and especially because one band of 3 TGR had disappeared a new recombination event must have occurred in these cells.

The DGR proviruses from TRX-1 and TRX-2 were rescued and their V-J junctions were sequenced. Although the proviruses from TRX-1 and TRX-2 contained identical V-J junctions (deletion of two nucleotides from the J coding region, but no deletion of nucleotides from V), the sequences differed from that of the provirus of TR-1, confirming that an independent event occurred in the secondary transfection.

The presence of human repetitive DNA elements in the transfectants was investigated using gel transfer hybridization and the highly repetitive probe BLUR-8 (Rubin, C. M. et al., Nature, 284:372–374 (1980)), the middle repetitive probes T&G-C (Gusella, J. F. et al., Proc. Natl. Acad. Sci. USA, 79:7804–7808 (1982)) and pE40-10, a homolog of A35Fc (Gusella, J. F. et al., Proc. Natl. Acad. Sci. USA, 79:7804–7808 (1982)), or total human DNA. While the BLUR-8 and total human DNA probes hybridized with DNA from the primary transfectant TR-1, no hybridization was detected with any of the probes with DNA from the recipient of the transfections, 3TGR, or with DNA from the secondary transfectants, TRX-1 and TRX-2. Because TR-1 contained both human and murine DNA, the lack of detectable human DNA in the secondary transfectants raised the possibility that the gene transferred in the secondary transfection was the murine homolog of the human gene that it was presumed was transferred to TR-1 in the primary transfection.

Equivalents

Those skilled in the art will recognize, or be able to ascertain, using no more that routine experimentation, many equivalents to the specific embodiments of the invention described specifically herein. Such equivalents are intended to be encompassed in the scope of the following claims.

We claim:

1. An isolated recombination activating gene of mammalian orgin.

2. A gene of claim 1 which is of human origin.

3. Isolated DNA of mammalian origin encoding recombinase.

4. Isolated DNA of mammalian origin capable of stably activating recombination of variable region gene segments in hematopoietic cells.

5. Isolated DNA having the nucleic acid sequence of FIG. 6.